US012558482B1

(12) United States Patent
Schiff et al.

(10) Patent No.: US 12,558,482 B1
(45) Date of Patent: Feb. 24, 2026

(54) SEALING SYSTEMS FOR A RESERVOIR OF AN ON-BODY INJECTOR

(71) Applicant: Fresenius Kabi Deutschland GmbH, Bad Homburg (DE)

(72) Inventors: David R. Schiff, Highland Park, NJ (US); Sharon D. West, Elkins Park, PA (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 748 days.

(21) Appl. No.: 17/935,321

(22) Filed: Sep. 26, 2022

Related U.S. Application Data

(62) Division of application No. 17/307,594, filed on May 4, 2021, now Pat. No. 11,484,646.

(51) Int. Cl.
| | |
|---|---|
| *A61M 5/168* | (2006.01) |
| *A61M 5/142* | (2006.01) |
| *A61M 5/145* | (2006.01) |

(52) U.S. Cl.
CPC .... *A61M 5/16881* (2013.01); *A61M 5/14248* (2013.01); *A61M 5/1454* (2013.01); *A61M 2005/14252* (2013.01)

(58) Field of Classification Search
CPC ............ A61M 5/1454; A61M 5/14248; A61M 5/16881; A61M 2005/14252
See application file for complete search history.

(56) References Cited

U.S. PATENT DOCUMENTS

| | | | | |
|---|---|---|---|---|
| 3,677,248 A | * | 7/1972 | McPhee | .................. A61M 5/36 |
| | | | | 222/416 |
| 4,072,149 A | | 2/1978 | Tischlinger | |

(Continued)

FOREIGN PATENT DOCUMENTS

| | | |
|---|---|---|
| EP | 2242034 A1 | 10/2010 |
| WO | 2018081234 A1 | 5/2018 |

(Continued)

OTHER PUBLICATIONS

Dexcom G6: Reusable Infiniflex Protective Overlay Guard Flexible Armor Case Cover. Etsy.com. https:..www.etsy.com/shop/OldsNewAgain?ref=simple-shop-header-name&listing_id=1081102727 (Year: 2021).

(Continued)

*Primary Examiner* — James D Ponton
(74) *Attorney, Agent, or Firm* — Cook Alex Ltd.

(57) ABSTRACT

An on-body injector includes a drug reservoir having an outlet. First and second pistons may be positioned within the reservoir, with the second piston first being moved to open the outlet, followed by the first piston being moved to convey a drug from the reservoir via the outlet. The reservoir may instead include a cover, with a valve positioned between the outlet and the cover. The valve is rotated to place a channel of the valve in fluid communication with a through-hole of the cover, allowing flow from the reservoir via the outlet. The reservoir may instead include a valve movable from a condition in which it deforms the outlet, preventing flow through the outlet, to a condition allowing flow. The reservoir may instead include a seal that is deformed by an increase in pressure within the reservoir, with the deformed seal being open to allow flow through the outlet.

19 Claims, 10 Drawing Sheets

(56)  References Cited

U.S. PATENT DOCUMENTS

| | | | |
|---|---|---|---|
| 4,234,104 | A | 11/1980 | Apuzzo, Jr. et al. |
| 4,878,646 | A * | 11/1989 | Edelman ............... A61M 39/28 |
| | | | 251/9 |
| 4,970,502 | A | 11/1990 | Kunikane et al. |
| 5,797,881 | A * | 8/1998 | Gadot ................... A61M 5/148 |
| | | | 604/153 |
| 6,620,134 | B1 | 9/2003 | Trombley, III et al. |
| 7,981,102 | B2 | 7/2011 | Patel et al. |
| 8,285,328 | B2 | 10/2012 | Caffey et al. |
| 9,452,255 | B2 | 9/2016 | Tieck et al. |
| 2002/0169439 | A1 | 11/2002 | Flaherty |
| 2003/0088238 | A1 | 5/2003 | Poulsen et al. |
| 2003/0167036 | A1 | 9/2003 | Flaherty |
| 2004/0068230 | A1 | 4/2004 | Estes et al. |
| 2004/0116866 | A1 | 6/2004 | Gorman et al. |
| 2004/0199123 | A1 | 10/2004 | Nielsen |
| 2006/0111671 | A1 | 5/2006 | Klippenstein |
| 2007/0290012 | A1 | 12/2007 | Jackman |
| 2008/0091139 | A1 | 4/2008 | Srinivasan et al. |
| 2008/0269657 | A1 | 10/2008 | Brenneman et al. |
| 2009/0131860 | A1 | 5/2009 | Nielsen |
| 2009/0156990 | A1 | 6/2009 | Wenger et al. |
| 2010/0130931 | A1 | 5/2010 | Yodfat et al. |
| 2011/0060196 | A1 | 3/2011 | Stafford |
| 2011/0178461 | A1 | 7/2011 | Chong et al. |
| 2011/0196304 | A1 | 8/2011 | Kramer et al. |
| 2012/0010594 | A1* | 1/2012 | Holt .................. A61M 5/14248 |
| | | | 604/151 |
| 2013/0006213 | A1 | 1/2013 | Arnitz et al. |
| 2015/0119804 | A1 | 4/2015 | Seeley et al. |
| 2015/0306307 | A1 | 10/2015 | Cole et al. |
| 2015/0374919 | A1 | 12/2015 | Gibson |
| 2016/0038689 | A1 | 2/2016 | Lee et al. |
| 2016/0082182 | A1 | 3/2016 | Gregory et al. |
| 2016/0175515 | A1 | 6/2016 | McCullough |
| 2016/0199574 | A1 | 7/2016 | Ring et al. |
| 2016/0220798 | A1 | 8/2016 | Netzel et al. |
| 2016/0296704 | A1 | 10/2016 | Gibson |
| 2016/0354555 | A1 | 12/2016 | Gibson et al. |
| 2016/0374707 | A1 | 12/2016 | Akagane |
| 2017/0119969 | A1 | 5/2017 | McCullough et al. |
| 2017/0124284 | A1 | 5/2017 | McCullough et al. |
| 2017/0147787 | A1 | 5/2017 | Albrecht et al. |
| 2017/0182253 | A1 | 6/2017 | Folk et al. |
| 2017/0312454 | A1 | 11/2017 | Chattaraj et al. |
| 2017/0340837 | A1 | 11/2017 | Nazzaro et al. |
| 2017/0361015 | A1 | 12/2017 | McCullough |
| 2017/0368260 | A1 | 12/2017 | McCullough et al. |
| 2018/0021508 | A1 | 1/2018 | Destefano et al. |
| 2018/0028747 | A1 | 2/2018 | Hanson et al. |
| 2018/0036476 | A1 | 2/2018 | McCullough et al. |
| 2018/0085517 | A1 | 3/2018 | Laurence et al. |
| 2018/0193554 | A1 | 7/2018 | Meehan et al. |
| 2018/0193557 | A1 | 7/2018 | Johnson et al. |
| 2018/0256823 | A1 | 9/2018 | Nazzaro et al. |
| 2018/0272059 | A1 | 9/2018 | Marbet et al. |
| 2018/0304014 | A1 | 10/2018 | Knudsen et al. |
| 2019/0009019 | A1 | 1/2019 | Shor et al. |
| 2019/0022306 | A1 | 1/2019 | Gibson et al. |
| 2019/0050375 | A1 | 2/2019 | Fitzgibbon et al. |
| 2019/0060562 | A1 | 2/2019 | Olivas et al. |
| 2019/0083702 | A1 | 3/2019 | Nekouzadeh et al. |
| 2019/0134296 | A1 | 5/2019 | Barbedette et al. |
| 2019/0143043 | A1 | 5/2019 | Coles et al. |
| 2019/0143047 | A1 | 5/2019 | Jazayeri et al. |
| 2019/0151544 | A1 | 5/2019 | Stonecipher |
| 2019/0167899 | A1 | 6/2019 | Cabiri |
| 2019/0167908 | A1 | 6/2019 | Fitzgibbon et al. |
| 2019/0192766 | A1 | 6/2019 | Stonecipher |
| 2019/0247579 | A1 | 8/2019 | Damestani et al. |
| 2019/0275241 | A1 | 9/2019 | Ring et al. |
| 2019/0282752 | A1* | 9/2019 | Franke .............. A61M 5/14248 |
| 2019/0321544 | A1 | 10/2019 | List |
| 2019/0328965 | A1 | 10/2019 | Moberg |
| 2019/0365986 | A1 | 12/2019 | Coiner et al. |
| 2019/0374707 | A1 | 12/2019 | Damestani et al. |
| 2019/0381238 | A1 | 12/2019 | Stonecipher et al. |
| 2020/0023122 | A1 | 1/2020 | McCullough et al. |
| 2020/0086044 | A1 | 3/2020 | Streit et al. |
| 2020/0164145 | A1 | 5/2020 | Chang et al. |
| 2020/0164155 | A1 | 5/2020 | Mojarrad et al. |
| 2020/0169439 | A1 | 5/2020 | Kim et al. |
| 2020/0179609 | A1 | 6/2020 | Tan-Malecki et al. |
| 2020/0197628 | A1 | 6/2020 | McCullough et al. |
| 2020/0206429 | A1 | 7/2020 | Hering et al. |
| 2020/0230313 | A1 | 7/2020 | Mojarrad et al. |
| 2020/0238004 | A1 | 7/2020 | McCullough |
| 2020/0254172 | A1 | 8/2020 | Forster et al. |
| 2020/0254185 | A1 | 8/2020 | Bar-el et al. |
| 2020/0261643 | A1 | 8/2020 | Boyaval et al. |
| 2020/0261648 | A1 | 8/2020 | Groszmann et al. |
| 2020/0261657 | A1 | 8/2020 | Gibson et al. |
| 2020/0289745 | A1 | 9/2020 | Harris et al. |
| 2020/0297927 | A1 | 9/2020 | Conrath et al. |
| 2020/0315918 | A1 | 10/2020 | Naygauz |
| 2020/0322793 | A1 | 10/2020 | Yang |
| 2020/0338271 | A1 | 10/2020 | Harris et al. |
| 2021/0228799 | A1 | 7/2021 | Streit et al. |

FOREIGN PATENT DOCUMENTS

| | | | |
|---|---|---|---|
| WO | 2018183039 | A1 | 10/2018 |
| WO | 2018226565 | A1 | 12/2018 |
| WO | 2019018169 | A1 | 1/2019 |
| WO | 2019022950 | A1 | 1/2019 |
| WO | 2019022951 | A1 | 1/2019 |
| WO | 2019032101 | A1 | 2/2019 |
| WO | 2019143753 | A1 | 7/2019 |

OTHER PUBLICATIONS

Omnipod Grip Shield Designed by Deck My Diabetes; Amazon. Available for sale Dec. 14, 2020 https://www.amazon.com/Deck-My-Diabetes-Flexible-Additional/dp/B08QL3TVZB/ref=sr_1_6?keywords=insulin+pump+overlay&qid=1639074568&sr=8-6 (Year: 2020).

RightCare CGM Adhesive Universal Overpatches; Amazon available for sale May 6, 2020. https://www.amazon.com/Adhesive-Universal-Covered-Synthetic-Extreme/dp/B083QMYXQ7/ref=sr_1_27?keywords=overpatch&qid=163080153&sr=8-27&th=1 (Year: 2020).

* cited by examiner

SEALING SYSTEMS FOR A RESERVOIR OF AN ON-BODY INJECTOR

CROSS-REFERENCE TO RELATED APPLICATIONS

This application is a division of U.S. patent application Ser. No. 17/307,594, filed May 4, 2021, the contents of which are hereby incorporated by reference herein.

BACKGROUND

Field of the Disclosure

The present disclosure relates to drug delivery devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, the reservoir may be provided with differently configured sealing systems, with different configurations providing different advantages compared to the configuration of the sealing system of a conventional device.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an on-body injector includes a housing, an adhesive pad associated with a lower surface of the housing and configured to be removably attached to a human body surface, and a drug reservoir positioned within the housing and including an outlet. First and second pistons are positioned within the drug reservoir. The on-body injector further includes a needle fluidically connected to the outlet of the drug reservoir and a controller configured to control the components of the on-body injector to execute a drug delivery routine. The second piston is configured to be moved from a first position in which it prevents fluid flow from the drug reservoir via the outlet to a second position in which it allows fluid flow from the drug reservoir via the outlet. The first piston is configured to be moved with respect to the second piston in the second position to convey a drug out of the drug reservoir via the outlet during a drug delivery routine.

In another aspect, an on-body injector includes a housing, an adhesive pad associated with a lower surface of the housing and configured to be removably attached to a human body surface, and a drug reservoir positioned within the housing and including an outlet. A cover defining a through-hole is associated with the reservoir, with a valve at least partially positioned between the outlet of the drug reservoir and the cover. The on-body injector also includes a needle is fluidically connected to the outlet of the drug reservoir and a controller configured to control the components of the on-body injector to execute a drug delivery routine. The valve defines a channel and is configured to be rotated from a first position in which the channel is not oriented to allow fluid flow from the through-hole to the outlet to a second position in which the channel is oriented to allow fluid flow from the through-hole to the outlet.

In yet another aspect, an on-body injector includes a housing, an adhesive pad associated with a lower surface of the housing and configured to be removably attached to a human body surface, and a drug reservoir positioned within the housing and including a deformable outlet having an associated valve. A needle is fluidically connected to the outlet of the drug reservoir, while a controller is configured to control the components of the on-body injector to execute a drug delivery routine. The valve is configured to be moved from a first condition in which it engages and deforms the outlet so as to prevent fluid flow from the drug reservoir via the outlet and a second condition in which the valve is at least partially disengaged from the outlet so as to allow fluid flow from the drug reservoir via the outlet.

In another aspect, an on-body injector includes a housing, with an adhesive pad associated with a lower surface of the housing and configured to be removably attached to a human body surface. A drug reservoir is positioned within the housing and includes an outlet and a seal, which is at least partially positioned within the drug reservoir. A needle is fluidically connected to the outlet of the drug reservoir, while a controller is configured to control the components of the on-body injector to execute a drug delivery routine. The seal is configured to be deformed from a first condition to a second condition by an increase in pressure within the drug reservoir, with the seal preventing fluid flow from the drug reservoir via the outlet in the first condition and the seal being at least partially open in the second condition so as to allow fluid flow from the drug reservoir via the outlet.

These and other aspects of the present subject matter are set forth in the following detailed description of the accompanying drawings.

6

Figure 1:
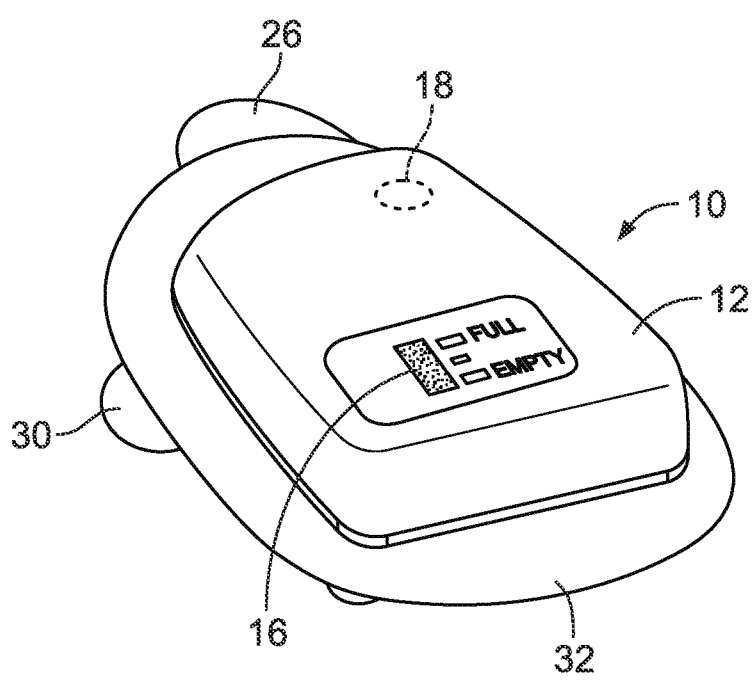
FIG. 1 is a top perspective view of a drug delivery device according to conventional design.
Figure 2:
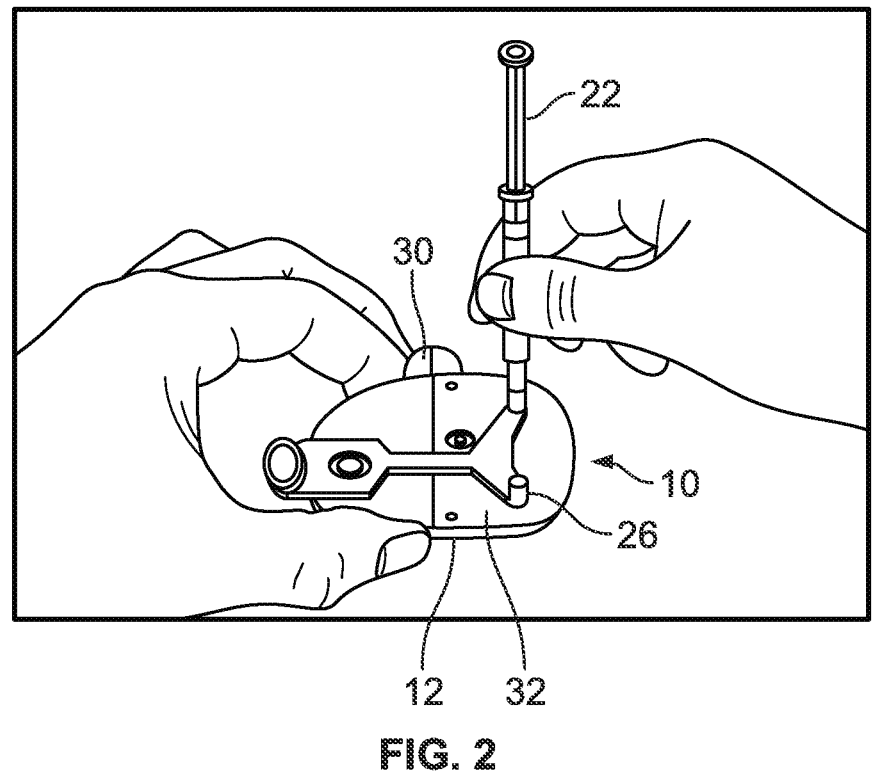
FIG. 2 is a bottom perspective view of the drug delivery device of FIG. 1.
Figure 3:
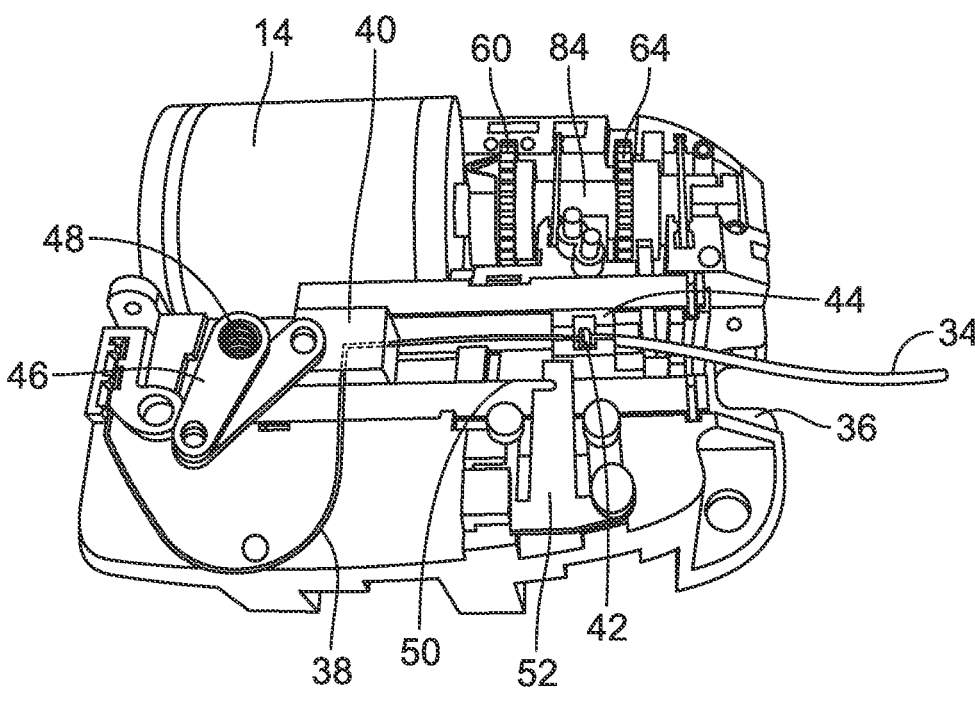
FIG. 3 is a top perspective view of the interior components of the drug delivery device of FIG. 1.
Figure 4:
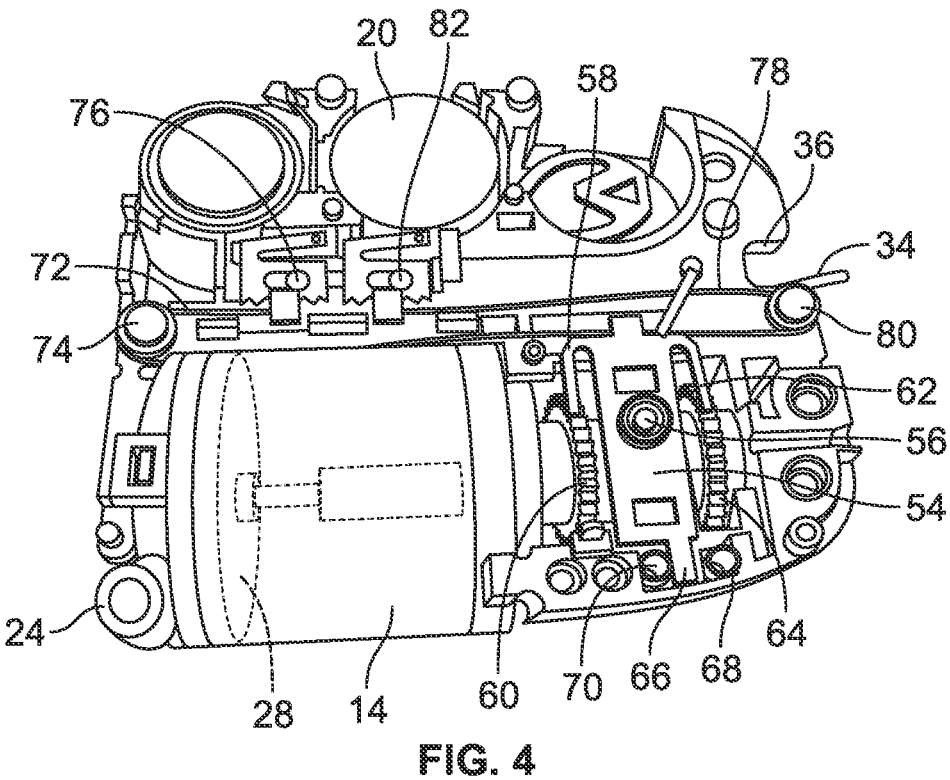
FIG. 4 is a bottom perspective view of the interior components of the drug delivery device of FIG. 1.
Figure 5:
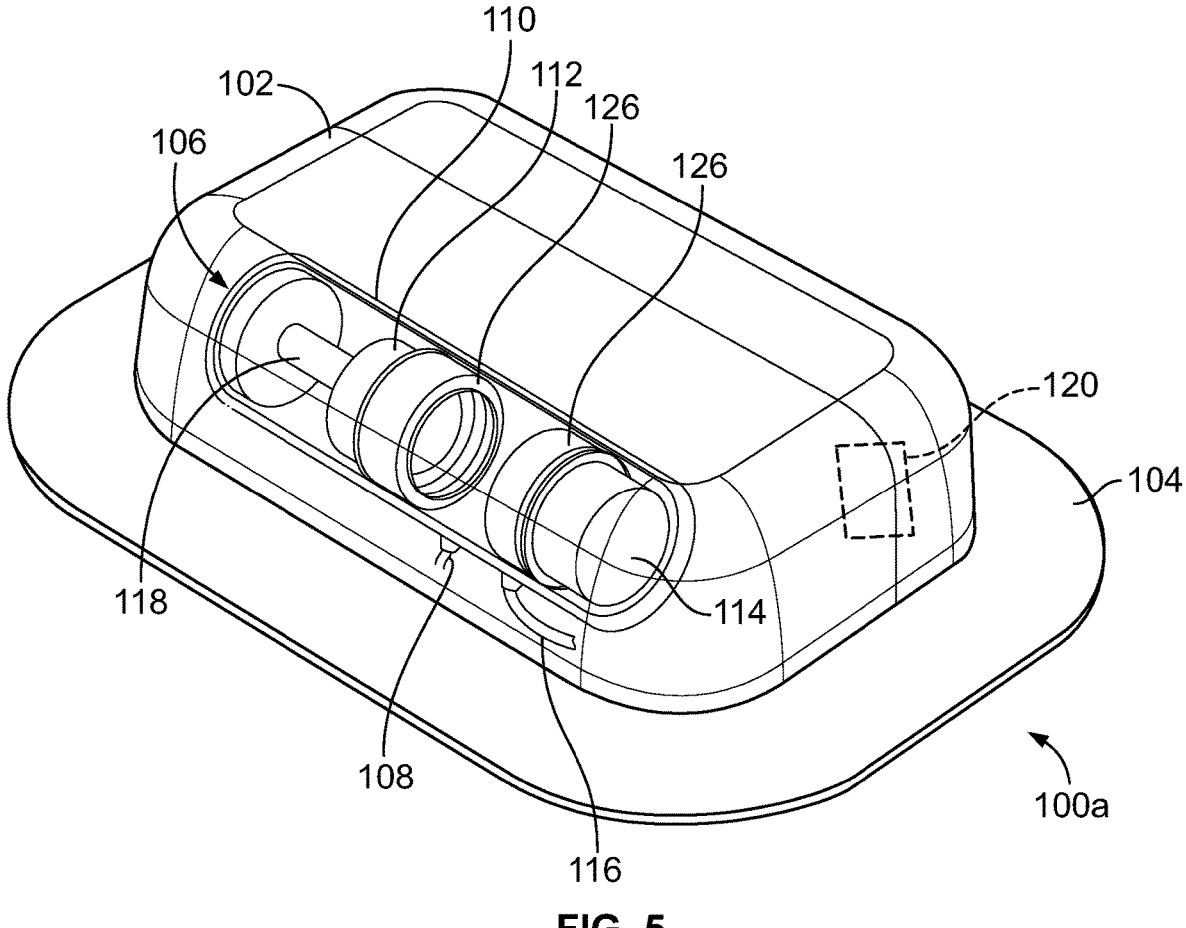
FIG. 5 is a perspective view of an exemplary embodiment of a reservoir and sealing system of an on-body injector according to an aspect of the present disclosure.
Figures 10, 11:
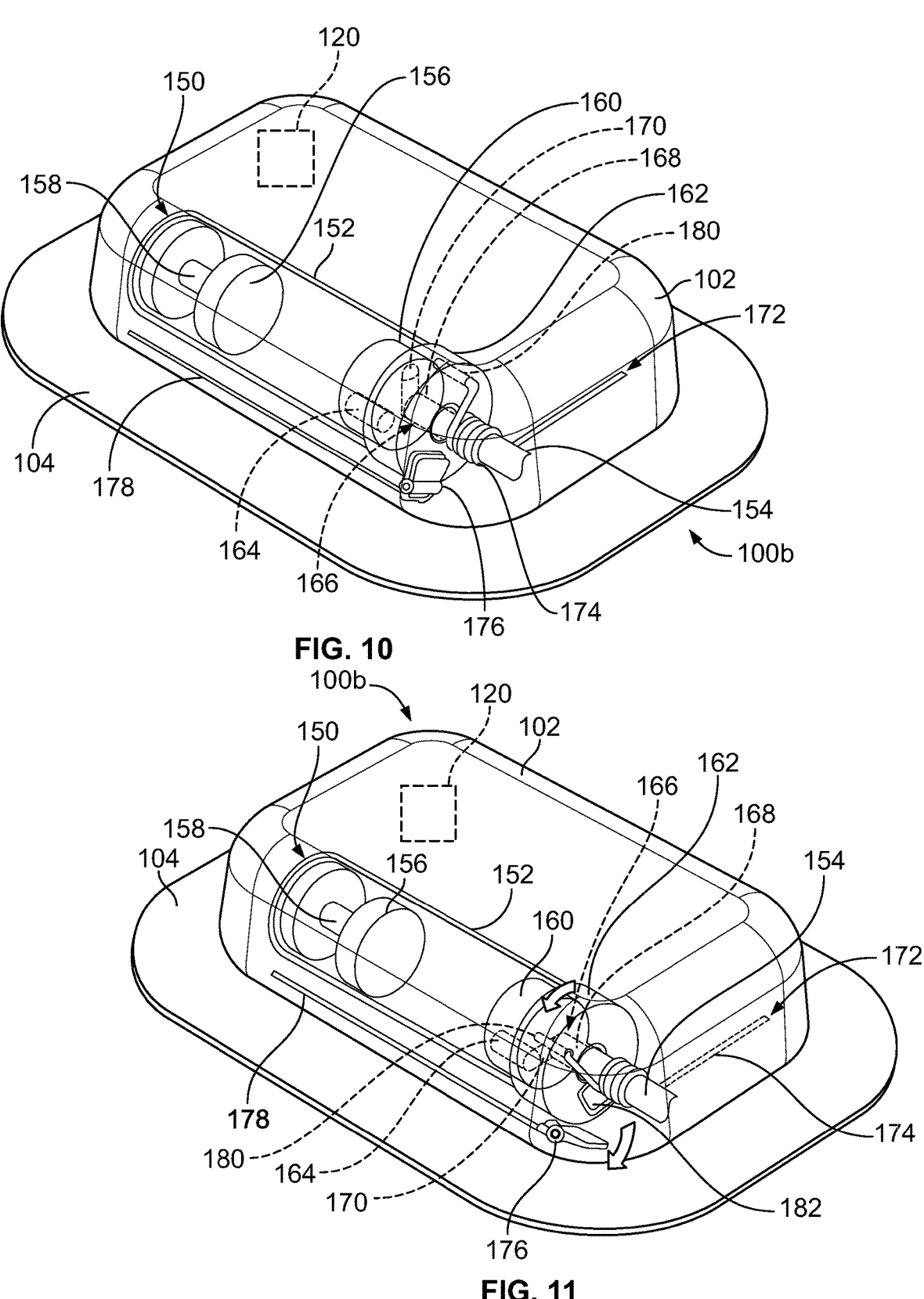
Figure 12:
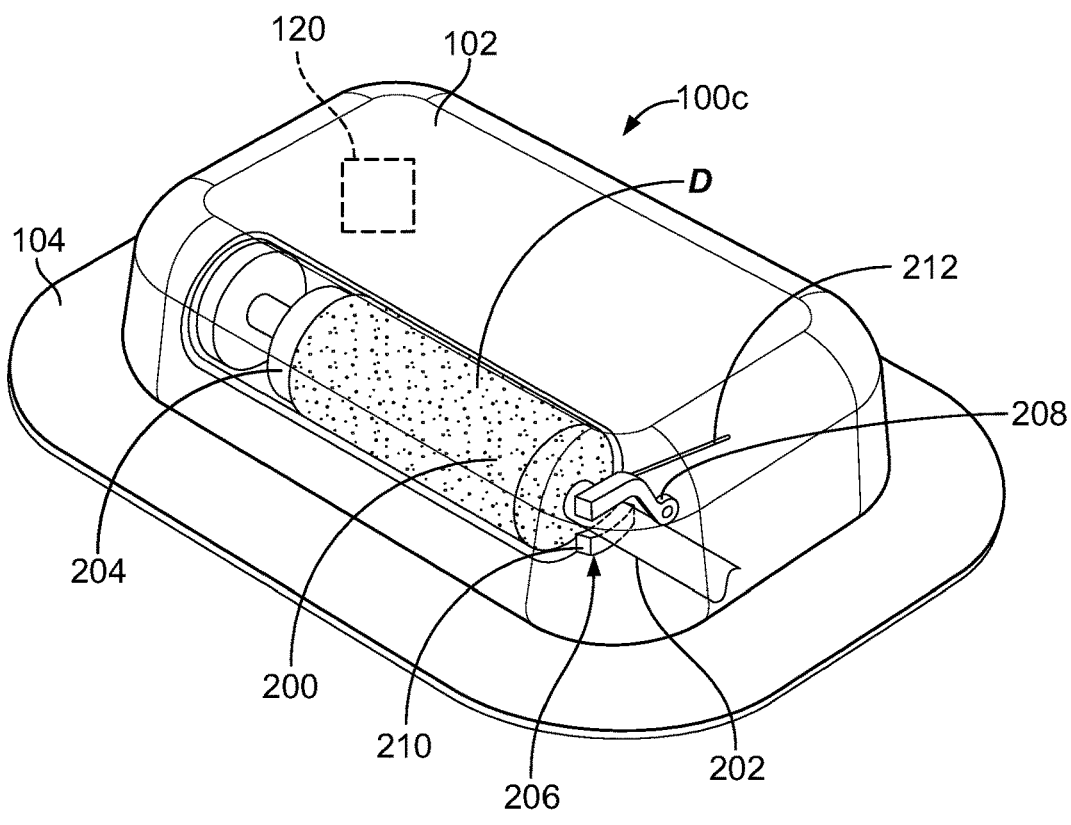
Figure 13:
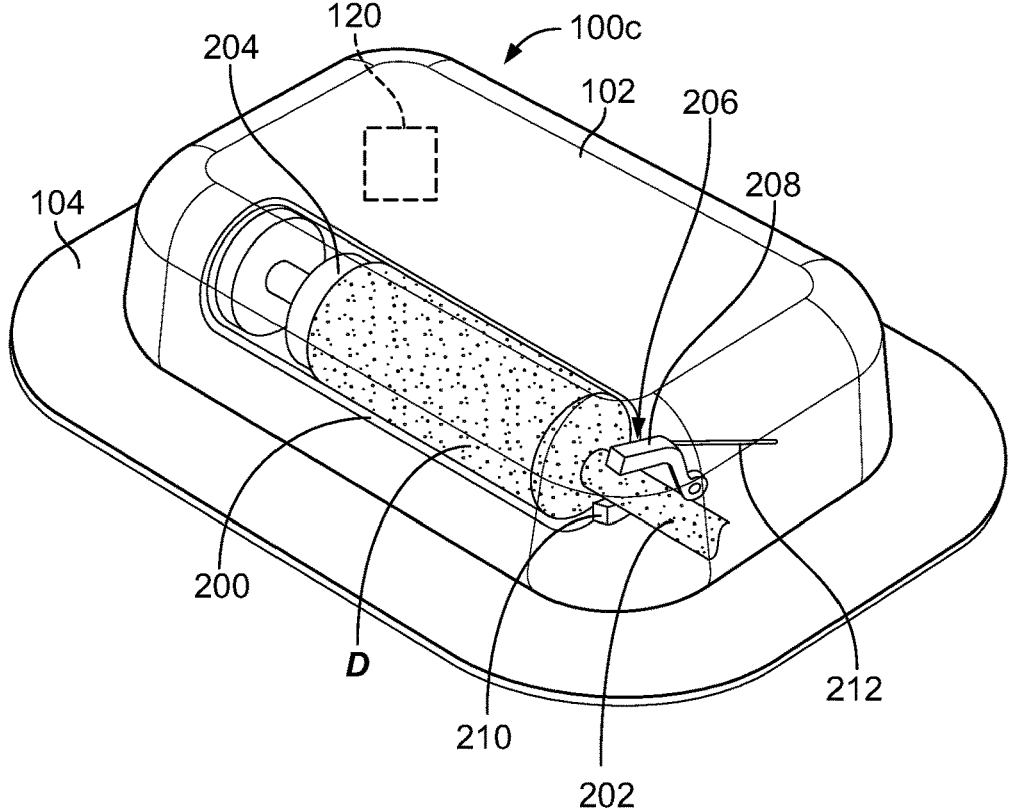
Figure 14:
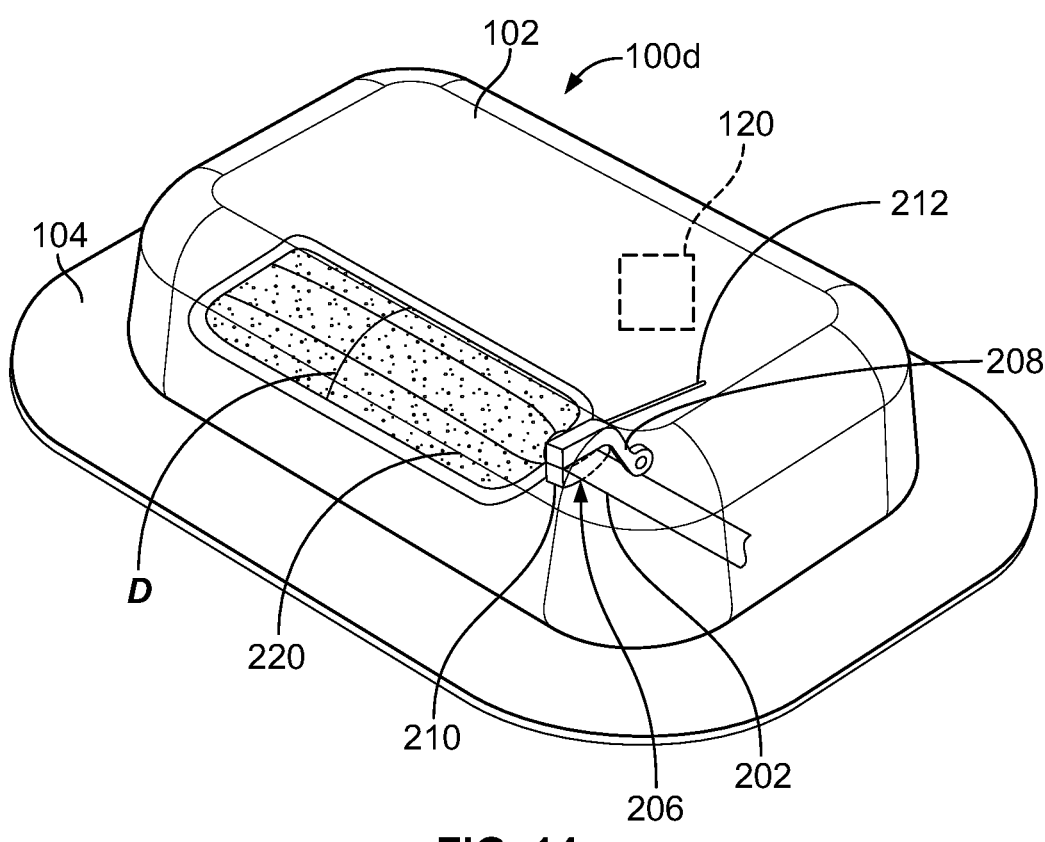
Figure 15:
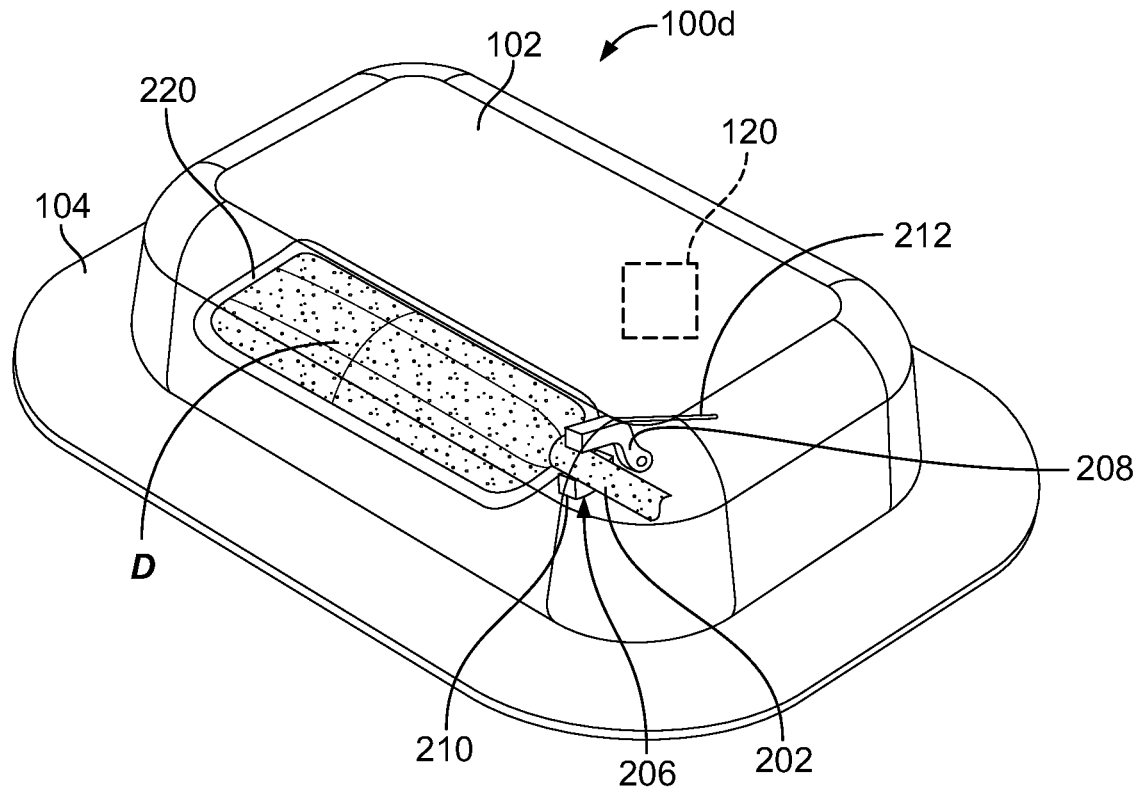
Figures 16, 17:
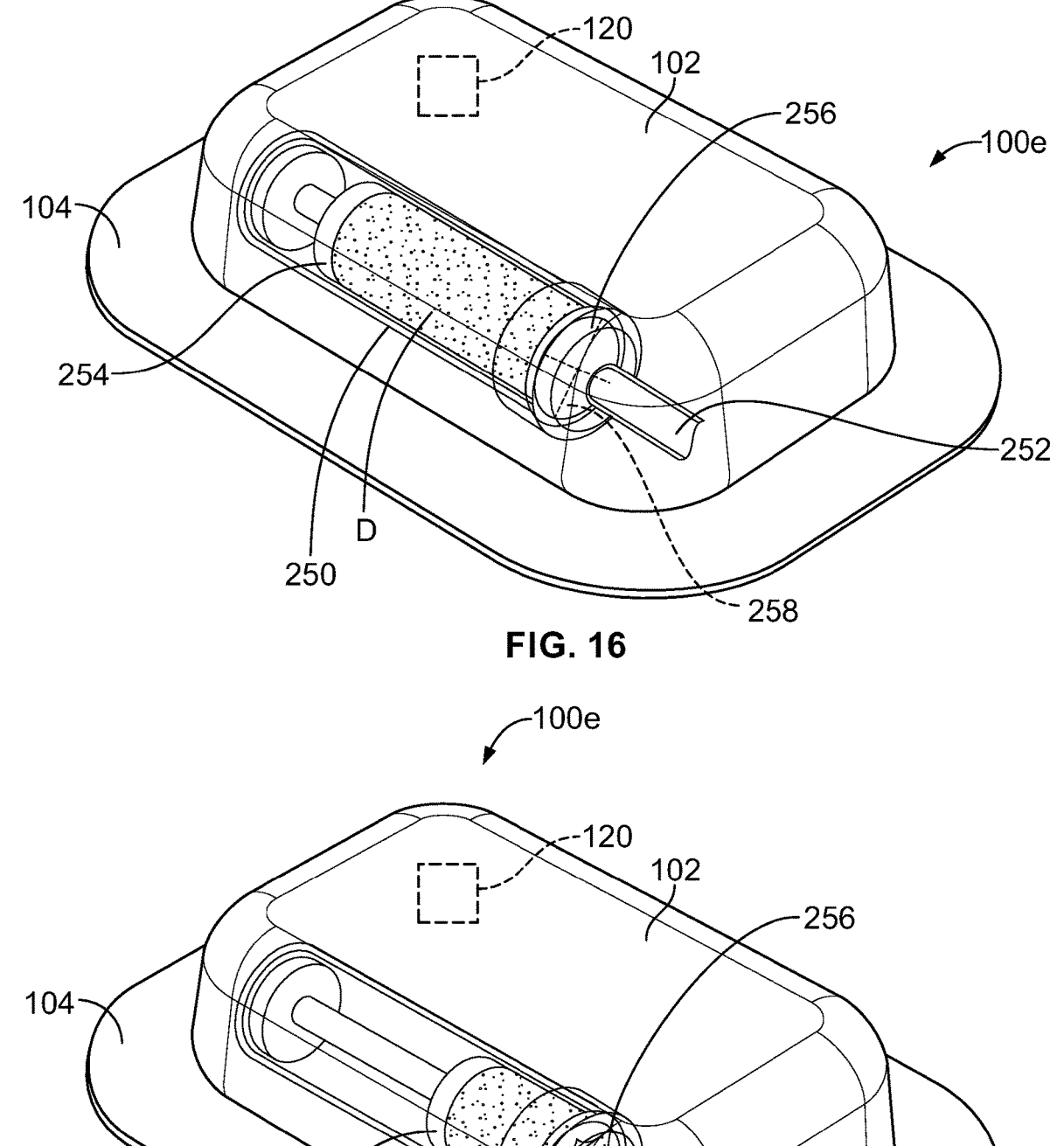
Figure 18:
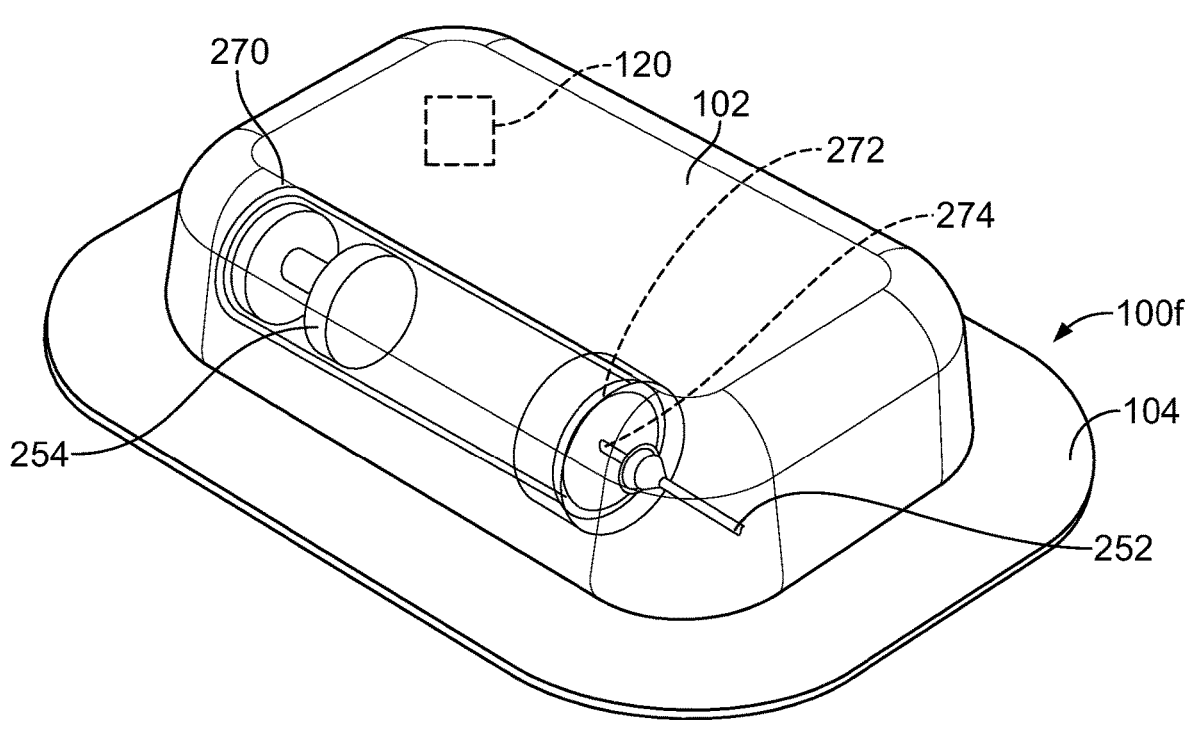
Figure 19:
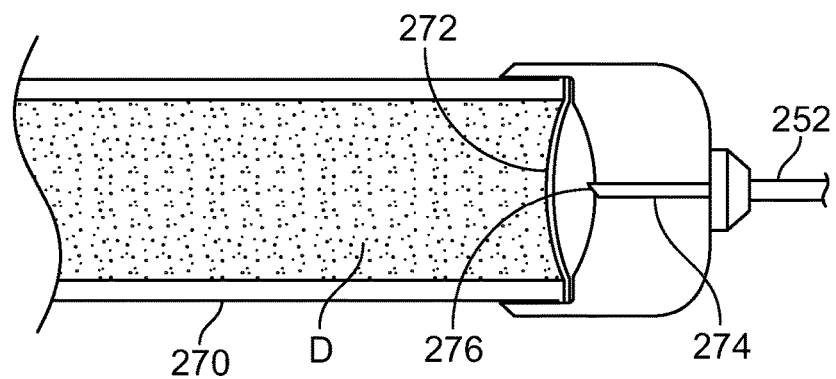
Figure 20:
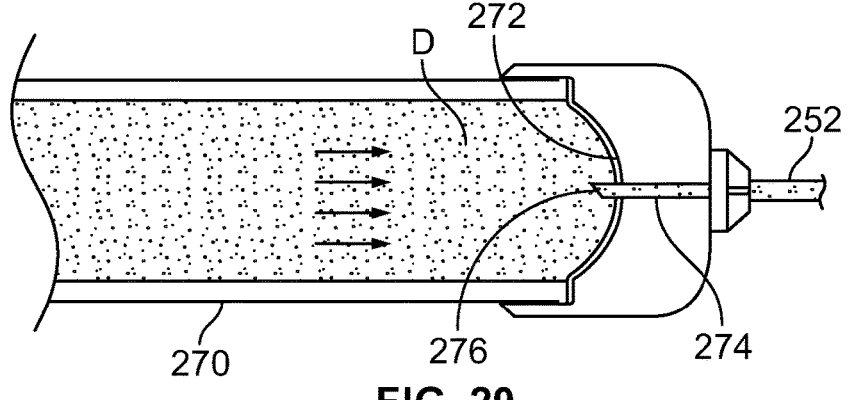
Figures 21, 22, 23:
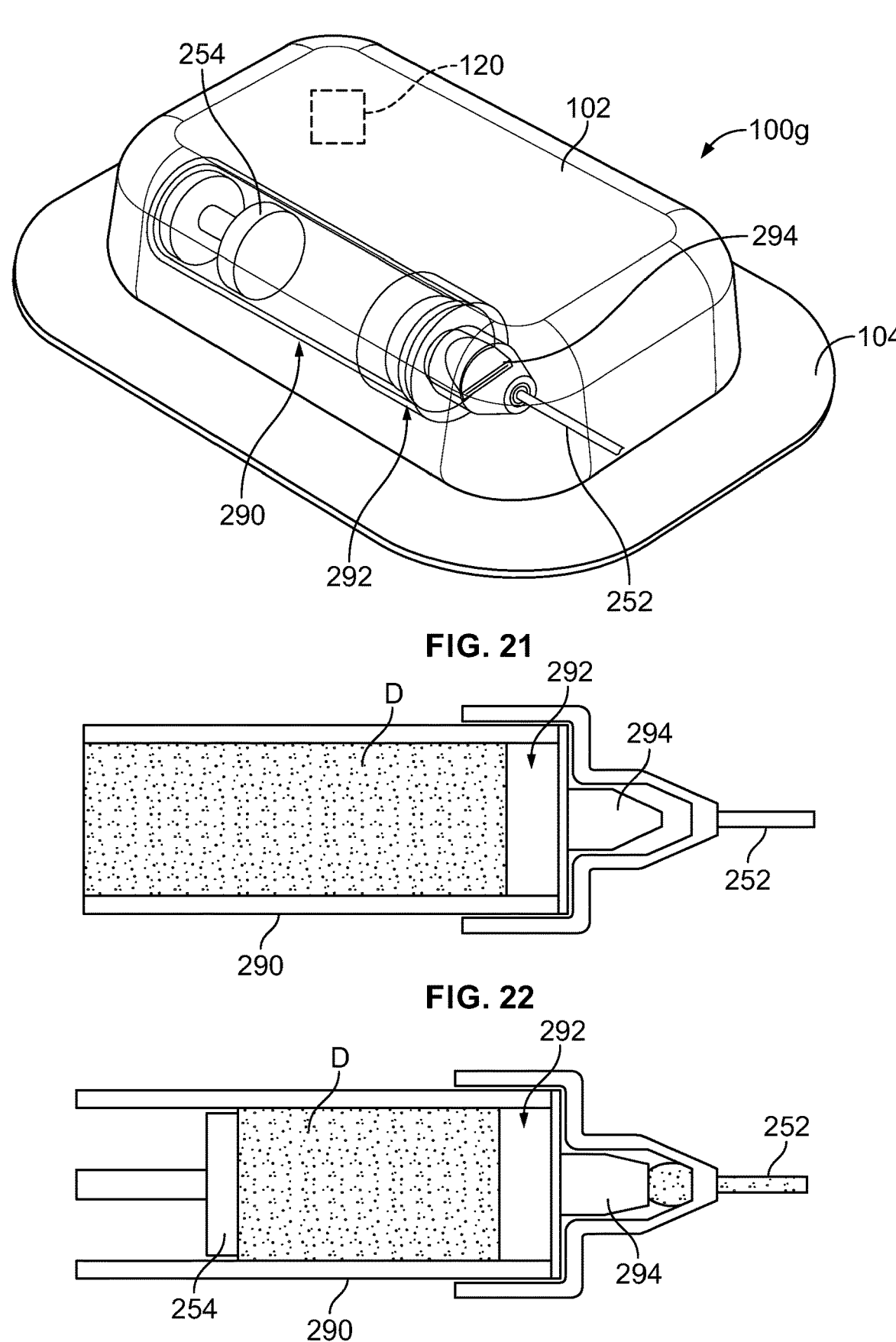

FIGS. 6-9 are cross-sectional views of the reservoir of FIG. 5, showing a process of filling the reservoir with a drug and then delivering the drug to a subject;

FIG. 10 is a perspective view of another exemplary embodiment of a reservoir and sealing system of an on-body injector according to an aspect of the present disclosure, with a valve in a closed condition;

FIG. 11 is a perspective view of the reservoir and sealing system of FIG. 10, with the valve in an open condition;

FIG. 12 is a perspective view of yet another exemplary embodiment of a reservoir and sealing system of an on-body injector according to an aspect of the present disclosure, with a valve in a closed condition;

FIG. 13 is a perspective view of the reservoir and sealing system of FIG. 12, with the valve in an open condition;

FIG. 14 is a perspective view of another exemplary embodiment of a reservoir and sealing system of an on-body injector according to an aspect of the present disclosure, with a valve in a closed condition;

FIG. 15 is a perspective view of the reservoir and sealing system of FIG. 14, with the valve in an open condition;

FIG. 16 is a perspective view of another exemplary embodiment of a reservoir and sealing system of an on-body injector according to an aspect of the present disclosure, with a seal in a closed condition;

FIG. 17 is a perspective view of the reservoir and sealing system of FIG. 16, with the seal in an open condition;

FIG. 18 is a perspective view of yet another exemplary embodiment of a reservoir and sealing system of an on-body injector according to an aspect of the present disclosure;

FIG. 19 is a cross-sectional view of the reservoir and sealing system of FIG. 18, with a seal in a closed condition;

FIG. 20 is a cross-sectional view of the reservoir and sealing system of FIG. 18, with the seal in an open condition;

FIG. 21 is a perspective view of another exemplary embodiment of a reservoir and sealing system of an on-body injector according to an aspect of the present disclosure;

FIG. 22 is a cross-sectional view of the reservoir and sealing system of FIG. 21, with a seal in a closed condition; and FIG. 23 is a cross-sectional view of the reservoir and sealing system of FIG. 21, with the seal in an open condition.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 5-23 illustrate exemplary embodiments of a drug reservoir and associated sealing system for an on-body injector embodying aspects of the present disclosure, whereby a drug in a reservoir is accessed by means other than piercing a septum. The on-body injectors 100a-100g of FIGS. 5-23 are not illustrated in detail, but rather only selected components are shown and described herein. It should be understood that the components not shown and/or described in detail herein may be provided according to any suitable configuration, which includes the components being configured and functioning as described above with regard to the conventional device 10 of FIGS. 1-4.

In the embodiment of FIGS. 5-9, the on-body injector 100*a* includes a housing 102 that contains or encloses the functional components of the on-body injector 100*a*. An adhesive pad 104 is associated with a lower surface of the housing 102 for removably attaching the on-body injector 100*a* to a human body surface (e.g., to an arm or an abdomen). A release film may be associated with the adhesive pad 104 and removed just prior to securing the adhesive pad 104 to the body of a patient, as described above with regard to the conventional device 10 of FIGS. 1-4.

A drug reservoir 106 is contained within the housing 102. The drug reservoir 106 is configured to contain a liquid drug "D", which may be injected therein via a port or inlet 108 (as described with regard to the device 10 of FIGS. 1-4) or may be provided therein by any suitable approach without departing from the scope of the present disclosure. The drug reservoir 106 includes a sidewall 110 formed of a generally rigid material that is configured to not deform as pressure within the drug reservoir 106 changes.

First and second pistons 112 and 114 are positioned within the drug reservoir 106, with the first piston 112 spaced away from an outlet 116 of the drug reservoir 106 (which is shown as being defined in the sidewall 110 of the drug reservoir 106) and the second piston positioned closer to the outlet 116. In the illustrated embodiment, the pistons 112 and 114 are substantially identical, though it should be understood that the second piston 114 may have a different configuration than the first piston 112. Regardless of the particular configurations of the pistons 112 and 114, they may be formed of different materials without departing from the scope of the present disclosure, which includes the pistons 112 and 114 being at least partially formed of an elastomeric material (e.g., a rubber material) or a generally rigid material (e.g., a plastic material or a metallic material).

Figures 6, 7, 8, 9:
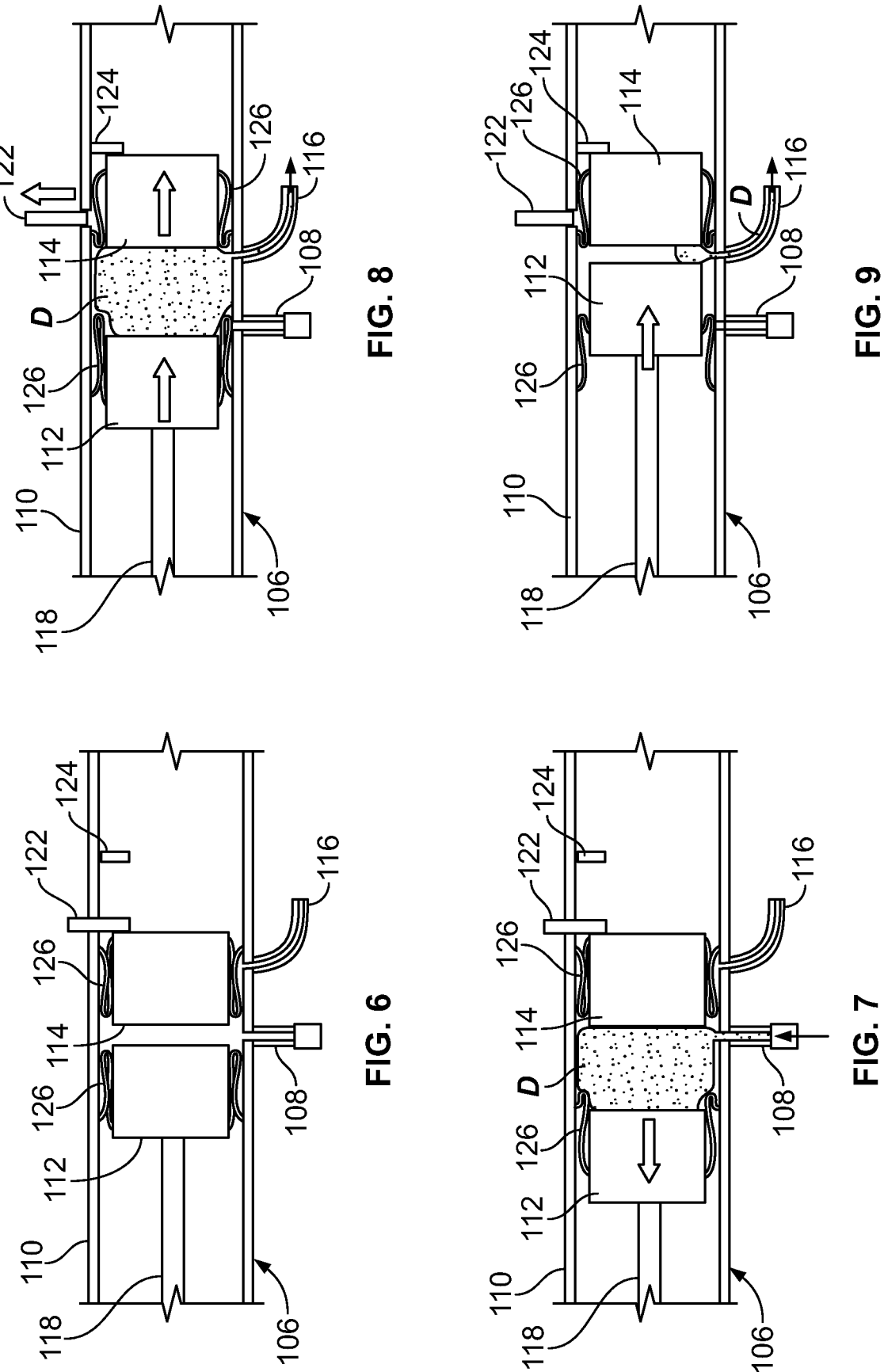

The pistons 112 and 114 define a space therebetween that is configured to receive a drug D (as shown in FIGS. 7-9), with each piston 112, 114 forming a seal with the inner surface of the sidewall 110 of the drug reservoir 106 to ensure that the drug D remains between the pistons 112 and 114 while in the drug reservoir 106. In the illustrated embodiment, the pistons 112 and 114 have circular profiles in order to form a seal with a generally cylindrical drug reservoir 106, but it should be understood that the pistons 112 and 114 may be differently configured without departing from the scope of the present disclosure.

Each piston 112, 114 is configured to move within the interior of the drug reservoir 106 in a direction defined by the sidewall 110 of the drug reservoir 106. In the illustrated embodiment, only the first piston 112 is provided with a drive mechanism (which is shown in FIGS. 5-9 as a piston rod 118), with movement of the second piston 114 typically being in response to movement of the first piston 112. While FIGS. 5-9 illustrate a drive mechanism configured as a piston rod 118 (which may be moved by a muscle wire and lever assembly of the type described above with regard to the device 10 of FIG. 1-4 in an exemplary embodiment), it should be understood that a differently configured drive mechanism may be employed without departing from the scope of the present disclosure. Additionally, while FIGS. 5-9 illustrate the second piston 114 as not having an associated drive mechanism, it should be understood that the second piston 114 may include a drive mechanism (which may be similarly configured to the drive mechanism of the first piston 112 or differently configured) without departing from the scope of the present disclosure.

In an exemplary embodiment, the first and second pistons 112 and 114 are initially positioned in the orientation of FIG.

6, with the second piston 114 forming a seal with the sidewall 110 that prevents fluid flow from the drug reservoir 106 into the outlet 116. The pistons 112 and 114 may be positioned as shown in FIG. 6 prior to use, in an as-manufactured condition.

In one embodiment, a drug D is injected into the space between the pistons 112 and 114 via the inlet 108, which causes the first piston 112 to move away from the second piston 114 to accommodate the drug D as it enters the drug reservoir 106 (FIG. 7). Alternatively, a controller 120 of the on-body injector 100*a* (which may be configured as described above with regard to the device 10 of FIGS. 1-4 or differently configured) may be configured to cause the drive mechanism 118 to move the first piston 112 away from the second piston 114 at a designated time. In this case, the movement of the first piston 112 from the position shown in FIG. 6 to the position shown in FIG. 7 reduces the pressure within the space between the pistons 112 and 114, which draws the drug D into the space via the inlet 108.

The nature of the drug D may vary without departing from the scope of the present disclosure, with on-body injectors according to the present disclosure being suitable for use in combination with a wide variety of liquid drugs or drug solutions. For example, in one embodiment, the methods and devices described herein are used to deliver pegfilgrastim to a subject. Other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

Regardless of the nature of the drug D, once it is positioned in the space between the pistons 112 and 114 (which may be the entire amount of the drug D to be conveyed to a subject or just a portion thereof), the on-body injector 100*a* is ready to deliver the drug D at the designated time. To do so, the controller 120 causes the drive mechanism 118 of the first piston 112 to move the first piston 112 toward the second piston 114 (FIG. 8). In the illustrated embodiment, the second piston 114 is held in its initial position by a first stop 122 extending into the interior of the drug reservoir 106. The configuration of the first stop 122 may vary without departing from the scope of the present disclosure, provided that it is configured to engage and prevent the second piston 114 from moving away from the first piston 112. In embodiments in which a first stop 122 is provided, the controller 120 may be configured to cause the first stop 122 to disengage the second piston 114 (e.g., by moving the first stop 122 out of the interior of the drug reservoir 106, as shown in FIG. 8) substantially simultaneously with causing the drive mechanism 118 to move the first piston 112 toward the second piston 114.

With the second piston 114 freed to move, movement of the first piston 112 toward the second piston 114 will cause both pistons 112 and 114 (along with the drug D positioned in the space between the pistons 112 and 114) to move in the direction of the outlet 116 (left-to-right in the orientation of FIG. 8). Eventually, the second piston 114 will move to the extent necessary to unseal the outlet 116, which places the drug D in the space between the pistons 112 and 114 into fluid communication with the outlet 116. In the illustrated embodiment, a second stop 124 extends into the interior of the drug reservoir 106 to engage the second piston 114 and prevent further movement of the second piston 114 in the direction in which it is being moved by the first piston 112. In an alternative embodiment, movement of the second piston 114 may be stopped by the second piston 114 coming into contact with an end of the drug reservoir 106 or by any other suitable arrangement.

While movement of the second piston 114 is prevented, the first piston 112 continues to advance toward the second piston 114 (FIG. 9). Continued movement of the first piston 112 toward the second piston 114 forces the drug D from the drug reservoir 106 via the outlet 116. It will be seen that, in the illustrated embodiment, the first piston 112 is positioned so as to overlay and seal the inlet 108, such that the drug reservoir 106 may not be refilled via the inlet 108.

From the outlet 116, the drug D moves through a fluid path defined within the on-body injector 100a until it is conveyed out of the on-body injector 100a and into the body of a patient via a needle fluidically connected to the drug reservoir 106. As described above with regard to the device 10 of FIGS. 1-4, a distal end of the needle may be sharpened or beveled for piercing the skin of a patient for drug delivery. As also described above, a flexible cannula may be associated with the needle, with the needle piercing the skin and then being withdrawn, while the distal end of the flexible cannula remains within the skin for drug delivery to the patient.

The nature of the seal between each piston 112, 114 and the inner surface of the sidewall 110 of the drug reservoir 106 may vary without departing from the scope of the present disclosure, provided that the pistons 112 and 114 are configured to move while the seals are maintained. In the illustrated embodiment, each piston 112, 114 is sealingly secured to the inner surface of the drug reservoir 106 by a rolling diaphragm 126, which may be advantageous to the extent that a rolling diaphragm will provide minimal resistance to movement of the pistons 112 and 114. While the illustrated embodiment shows the pistons 112 and 114 as having similarly configured seals, it should be understood that the seals of the pistons 112 and 114 may be differently configured without departing from the scope of the present disclosure.

FIGS. 10 and 11 illustrate another embodiment of an on-body injector 100b embodying aspects of the present disclosure. The on-body injector 100b may be similarly configured to the embodiment of FIGS. 5-9, except for a differently configured drug reservoir 150 and sealing system.

As in the embodiment of FIGS. 5-9, the drug reservoir 150 of FIGS. 10 and 11 includes a sidewall 152 formed of a generally rigid material that is configured to not deform as pressure within the drug reservoir 150 changes. FIGS. 10 and 11 do not illustrate an inlet (in which case the drug reservoir 150 is filled during manufacture of the device), but it should be understood that the drug reservoir 150 may be provided with an inlet, such as one of the type described above with regard to the embodiment of FIGS. 5-9. The drug reservoir 150 of FIGS. 10 and 11 also includes an outlet 154 but, rather than having an outlet defined in the sidewall 152 (as in the embodiment of FIGS. 5-9), the outlet 154 is instead associated with an end of the drug reservoir 150. A single piston 156 is positioned within the drug reservoir 150, adjacent to an opposite end of the drug reservoir 150. As in the embodiment of FIGS. 5-9, the piston 156 forms a seal with the sidewall 152 of the drug reservoir 150 and is configured to be moved through the interior of the drug reservoir 150 by a suitable drive mechanism (e.g., a piston rod 158) in a direction defined by the sidewall 152. The piston 156 may be formed of different materials without departing from the scope of the present disclosure, which includes the piston 156 being at least partially formed of an elastomeric material (e.g., a rubber material) or a generally rigid material (e.g., a plastic material or a metallic material).

The drug reservoir 150 of FIGS. 10 and 11 includes a cover 160 and a valve 162. The cover 160 is associated with the end of the drug reservoir 150 having the outlet 154, while at least a portion of the valve 162 is positioned between the cover 160 and the outlet 154. The cover 160 may be formed of any suitable material (e.g., a generally rigid plastic material) and is sealingly affixed to the sidewall 152 of the drug reservoir 150. The cover 160 is illustrated as being generally circular or cylindrical in shape (which may be advantageous when the drug reservoir 150 is generally cylindrical), but it should be understood that the cover 160 may be differently shaped without departing from the scope of the present disclosure. Regardless of the particular configuration of the cover 160, it defines an opening or through-hole 164 having an end that opens into the interior of the drug reservoir 150, with an opposite end positioned adjacent to the valve 162. FIGS. 10 and 11 illustrate a substantially straight or linear through-hole 164 that is oriented substantially parallel to (but not coaxial with) a central axis of the drug reservoir 150, though it is contemplated that the through-hole 164 may be differently shaped and positioned, provided that it defines a fluid flow path between the interior of the drug reservoir 150 and the valve 162.

As for the valve 162, it may be formed of any suitable material (e.g., a generally rigid plastic material) and is associated to the cover 160 with a fluid-tight seal to prevent a drug in the through-hole 164 from leaking out at the interface between the cover 160 and the valve 162. The valve 162 is illustrated as being generally circular or cylindrical in shape (which may be advantageous when the drug reservoir 150 and cover 160 are generally cylindrical), but it should be understood that the valve 162 may be differently shaped without departing from the scope of the present disclosure. Regardless of the particular configuration of the valve 162, it defines a passage or channel 166 having an end that opens into the outlet 154 of the drug reservoir 150, with an opposite end positioned adjacent to the cover 160. FIGS. 10 and 11 illustrate a channel 166 having an axially extending portion 168 (adjacent to the outlet 154) connected to a radially extending portion 170 (adjacent to the cover 160), though it is contemplated that the channel 166 may be differently shaped, provided that it is configured to be oriented so as to define a fluid flow path between the through-hole 164 of the cover 160 and the outlet 154 (FIG. 11).

The valve 162 is configured to be moved from a first or closed condition (FIG. 10) to a second or open condition (FIG. 11), with it being within the scope of the present disclosure for the valve 162 to be movable in the opposite direction, from the second or open condition to the first or closed condition. In the closed condition, the channel 166 is misaligned with the through-hole 164 and/or the outlet 154, which prevents a drug in the through-hole 164 from exiting the drug reservoir 150 via the outlet 154. In the open condition, the ends of the channel 166 are aligned with the through-hole 164 and the outlet 154, which allows a drug to flow from the interior of the drug reservoir 150, through the through-hole 164 of the cover 160, through the channel 166 of the valve 162, and out of the drug reservoir 150 via the outlet 154. In the illustrated embodiment, the valve 162 is configured to be rotated about a central axis (which coincides with the central axis of the drug reservoir 150 and a central axis of the outlet 154) from the closed condition to the open condition. In other embodiments, the valve 162 may be configured to move from the closed condition to the open condition in some other manner (e.g., by a sliding or translation motion).

More particularly, in the illustrated embodiment, the sealing system is provided with a drive assembly 172 configured to rotate the valve 162 from the closed condition to the open condition. The drive assembly 172 shown in FIGS. 10 and 11 includes a torsion spring 174, a latch 176, and a release mechanism 178. The torsion spring 174 is configured to bias the valve 162 toward the open condition, while the latch 176 is configured to prevent the torsion spring 174 from rotating the valve 162 to the open condition. The release mechanism 178 is configured to actuate or release the latch 176, which allows the torsion spring 174 to rotate the valve 162 into the open condition.

A free end 180 of the illustrated torsion spring 174 is secured to the valve 162, while the coiled body of the torsion spring 174 is wrapped around or encircles the outlet 154. The illustrated latch 176 is configured to selectively engage and disengage from the valve 162. The illustrated valve 162 includes a recess 182 (FIG. 11) in which at least a portion of the latch 176 is seated (FIG. 10) to prevent the valve 162 from being rotated to the open condition by the torsion spring 174. The release mechanism 178 (which is illustrated as a filament) manipulates the latch 176 to move at least a portion of the latch 176, which causes the latch 176 to move out of the recess 182 and disengage from the valve 162. The filament 178 may be variously configured, provided that it is configured to actuate the latch 176 at the designated time. In one exemplary embodiment, the filament 178 may be associated to the drive mechanism 158, with actuation of the drive mechanism 158 to move the piston 156 also moving or actuating the filament 178, causing the latch 176 to disengage the valve 162. In another exemplary embodiment, the filament 178 is configured as a muscle wire, formed of a shape memory alloy that contracts when heated. Heat may be applied by any suitable source, with heat being applied by an electrical current flowing through the filament 178 in an exemplary embodiment. When the filament 178 contracts, it pulls on the latch 176, causing the latch 176 to disengage the valve 162, followed by the valve 162 being rotated to its open condition by the torsion spring 174.

Thus, during a drug delivery routine, the controller 120 of the on-body injector 100b will actuate the filament 178 at the designated time, such as by causing an electrical current to be applied to the filament 178. The filament 178 contracts, which disengages the latch 176 from the valve 162. The torsion spring 174 rotates the valve 162 from the closed condition (FIG. 10) to the open condition (FIG. 11), which places the through-hole 164 of the cover 160 in fluid communication with the outlet 154. The controller 120 then causes the piston 156 to be moved toward the outlet 154 of the drug reservoir 150. Continued movement of the piston 156 toward the outlet 154 forces the drug through the through-hole 164 of the cover 160, through the channel 166 of the valve 162, and then out of the drug reservoir 150 via the outlet 154. From the outlet 154, the drug moves through a fluid path defined within the on-body injector 100b until it is conveyed out of the on-body injector 100b and into the body of a patient via a needle fluidically connected to the drug reservoir 150.

FIGS. 12 and 13 illustrate another embodiment of an on-body injector 100c embodying aspects of the present disclosure. The on-body injector 100c may be similarly configured to the embodiment of FIGS. 10 and 11, with a drug reservoir 200 having an outlet 202 at one end, with a piston 204 positioned within the drug reservoir 200 adjacent to an opposite end of the drug reservoir 200. However, in the embodiment of FIGS. 12 and 13 the drug reservoir 200 does not include a cover or a valve, but rather the outlet 202 opens directly into the interior of the drug reservoir 200.

In place of the cover and valve of FIGS. 10 and 11, the on-body injector 100c is instead provided with an outlet 202 at least partially formed of a deformable material (e.g., an elastomeric material, such as polyvinyl chloride). Due to the outlet 202 being deformable, it may be moved from a closed condition (FIG. 12) in which it is deformed (e.g., pinched shut) to prevent fluid flow through the outlet 202 to an open condition (FIG. 13) in which it is in its initial, non-deformed state, defining an open lumen allowing fluid flow therethrough. In addition to being capable of moving from the closed condition to the open condition, the outlet 202 may also be configured to be moved from the open condition to the closed condition.

A valve 206 is associated with the outlet 202 to move the outlet 202 from the closed condition to the open condition. The valve 206 may be variously configured without departing from the scope of the present disclosure, provided that it is suitable for moving the associated outlet 202 from the closed condition to the open condition. As such, it will be understood that the configuration of the valve 206 is dependent upon the configuration of the outlet 202. In the illustrated embodiment, the outlet 202 is configured as a deformable tube, which may be closed by pressing a portion of the wall of the tube against an opposing portion of the wall (i.e., pinching the tube shut). The valve 206 of FIGS. 12 and 13 is illustrated as having first and second jaws 208 and 210, which are pivotal with respect to each other, with a portion of the outlet 202 being positioned between the jaws 208 and 210. The jaws 208 and 210 may be biased (e.g., by a torsion spring) to pivot toward each other, which causes the jaws 208 and 210 to contact and deform the outlet 202, placing it in the deformed or closed condition of FIG. 12.

One of the jaws 208 is associated to a release mechanism 212, which selectively manipulates the associated jaw 208 to cause the jaw 208 to pivot away from the other jaw 210. This causes the valve 206 to at least partially disengage from the outlet 202, placing the outlet 202 in its open condition and allowing fluid flow through the outlet 202. The release mechanism 212 may be variously configured, provided that it is configured to actuate the valve 206 at the designated time. In the illustrated embodiment, the release mechanism 212 is configured as in the embodiment of FIGS. 10 and 11, which is as a filament or muscle wire, formed of a shape memory alloy that contracts when heated. As described above, heat may be applied by any suitable source, with heat being applied by an electrical current flowing through the filament 212 in an exemplary embodiment. When the filament 212 contracts, it pulls on the jaw 208, causing the jaw 208 to at least partially disengage from the outlet 202, which moves the outlet 202 to its open condition (FIG. 13).

Thus, during an exemplary drug delivery routine, the controller 120 of the on-body injector 100c will cause an electrical current to be applied to the filament 212 at the designated time. The filament 212 contracts, which at least partially disengages the valve 206 from the outlet 202, moving the outlet 202 from the closed condition (FIG. 12) to the open condition (FIG. 13). The controller 120 then causes the piston 204 to be moved toward the outlet 202 of the drug reservoir 200, with continued movement of the piston 204 toward the outlet 202 forcing the drug D out of the drug reservoir 200 via the outlet 202. From the outlet 202, the drug D moves through a fluid path defined within the on-body injector 100*c* until it is conveyed out of the on-body injector 100*c* and into the body of a patient via a needle fluidically connected to the drug reservoir 200.

It should be understood that the configuration of the drug reservoir 200 shown in FIGS. 12 and 13 is merely exemplary and that the drug reservoir may be differently configured without departing from the scope of the present disclosure. For example, FIGS. 14 and 15 illustrate an on-body injector 100*d* that is a variation of the on-body injector 100*c* of FIGS. 12 and 13. As described above, the drug reservoir 200 of FIGS. 12 and 13 is formed of a generally rigid material, with a piston 204 configured to be moved through the interior of the drug reservoir 200 to convey a drug out of the drug reservoir 200 via the outlet 202. In contrast, FIGS. 14 and 15 illustrate a drug reservoir 220 formed of a generally flexible or deformable material (e.g., an elastomeric material, such as polyvinyl chloride).

In the embodiment of FIGS. 14 and 15, force is applied to the drug reservoir 220 to compress or deform it, which causes a drug to be conveyed out of the drug reservoir 220 via the outlet 202. The force may be applied to the drug reservoir 220 before or after the valve 206 is opened. For example, the interior of the housing 102 may be pressurized, which causes a force to be applied to the drug reservoir 220 before the outlet 202 is opened. When the outlet 202 is opened, the drug reservoir 220 will be compressed and the drug D will be automatically conveyed out of the drug reservoir 220 via the outlet 202. In another example, the drug reservoir 220 may be deformed by physical contact, such as by placing at least a portion of the drug reservoir 220 between two surfaces (e.g., two flat plates) that may be moved relative to each other. The two surfaces may initially be spaced sufficiently far apart so as to not apply force to the drug reservoir 220 before the outlet 202 is opened. Once the outlet 202 has been opened, one or both of the surfaces may be moved toward the other surface, which applies a compressive force to the drug reservoir 220 and conveys the drug D from the drug reservoir 220 via the outlet 202.

FIGS. 16 and 17 illustrate another on-body injector 100*e* embodying aspects of the present disclosure. The on-body injector 100*e* may be similarly configured to the embodiment of FIGS. 10 and 11, with a drug reservoir 250 having an outlet 252 at one end, with a piston 254 positioned within the drug reservoir 250 adjacent to an opposite end of the drug reservoir 250. However, in the embodiment of FIGS. 16 and 17 the drug reservoir 250 does not include a cover or a valve positioned between the interior of the drug reservoir 250 and the outlet 252, but rather a deformable seal 256 is positioned therebetween. Due to the seal 256 being deformable, it may be moved from a first or closed condition (FIG. 16) in which it forms a complete barrier between the interior of the drug reservoir 250 and the outlet 252 to prevent fluid flow out of the drug reservoir 250 via the outlet 252 to a second or open condition (FIG. 17) in which the seal 256 is at least partially open to allow fluid from the interior of the drug reservoir 250 to the outlet 252. In one embodiment, the seal 256 is not capable of returning to the closed condition from the open condition after it has been opened, which may be the case if the seal 256 is configured to deform by breaking or rupturing, as shown in FIG. 17. When the seal is so configured (i.e., as a "burstable" seal), it may be advantageous for it to be used in combination with an on-body injector in which a drug is to be continuously (rather than intermittently) conveyed from the drug reservoir during a drug delivery routine.

The configuration of the seal 256 and the manner in which it deforms may vary without departing from the scope of the present disclosure. In one embodiment, the seal 256 is at least partially formed of a material (e.g., thin metal film or foil) that is configured to be deformed by an increase in pressure within the drug reservoir 250. Pressure may be applied to the seal 256 by any of a variety of possible approaches, but in one embodiment, the pressure applied to deform the seal 250 arises when the piston 254 is moved toward the seal 256, which increases the pressure within the drug reservoir 250. The seal 256 may be processed or otherwise configured to have at least one weakened section 258 (FIG. 16) that will break or fracture at a lower pressure than other portions of the seal 256. This may be advantageous to reduce the pressure required to move the seal 256 from its closed condition to its open condition, along with providing more control over the manner in which the seal 256 breaks or fractures. If provided, the weakened section 258 may be variously configured without departing from the scope of the present disclosure. For example, the weakened section 258 may be configured as a scored or perforated or creased section of the seal 256 or as a section having a thickness that is less than the thickness of other portions of the seal 256.

Thus, during a drug delivery routine, the controller 120 of the on-body injector 100*e* will cause the piston 254 to be moved toward the seal 256 at the designated time. The pressure within the drug reservoir 250 increases, which deforms the seal 256 from its closed condition (FIG. 16) to its open condition (FIG. 17), placing the interior of the drug reservoir 250 into fluid communication with the outlet 252. Continued movement of the piston 254 toward the outlet 252 forces the drug D out of the drug reservoir 250 via the outlet 252. From the outlet 252, the drug D moves through a fluid path defined within the on-body injector 100*e* until it is conveyed out of the on-body injector 100*e* and into the body of a patient via a needle fluidically connected to the drug reservoir 250.

It should be understood that the configuration of the seal shown in FIGS. 16 and 17 is merely exemplary and that the seal may be differently configured without departing from the scope of the present disclosure. For example, FIGS. 18-20 illustrate an on-body injector 100*f* that is a variation of the on-body injector 100*e* of FIGS. 16 and 17. As described above, the seal 256 of FIGS. 16 and 17 may be formed of a material that is configured to deform and break or fracture on its own when pressure within the drug reservoir 250 increases to a sufficient level. In contrast, FIGS. 18-20 illustrate a drug reservoir 270 having a seal 272 that is configured to deform without breaking or fracturing on its own when pressure within the drug reservoir 270 is increased.

Rather than the seal 272 of FIGS. 18-20 being configured to deform and break on its own, a piercing element 274 is associated with or incorporated into the drug reservoir 270. The piercing element 274 includes an end 276 (which may be sharpened) that is configured to pierce, rupture, or otherwise open the seal 272 when the seal 272 is brought into contact with the end 276 with sufficient force. The seal 272 is initially spaced away from the end 276 of the piercing element 274 in its first or closed condition (FIG. 19). When the seal 272 is deformed to its second or open condition (FIG. 20) by an increase in pressure within the drug reservoir 270, it comes into contact with the end 276 of the piercing element 274, which pierces or ruptures or otherwise opens the seal 272, opening fluid flow through the seal 272. In the illustrated embodiment, the piercing element 274 is configured as a needle or cannula defining a lumen fluidically connected to the outlet 252, such that causing the piercing element 274 to pierce through the seal 272 allows a drug D in the interior of the drug reservoir 270 to flow into and through the lumen of the piercing element 274, then into the outlet 252.

FIGS. 21-23 illustrate another on-body injector 100g that may be understood as a variation of the on-body injectors 100e and 100f of FIGS. 16-20. In the embodiment of FIGS. 21-23, the drug reservoir 290 has a seal 292 is configured to deform from a first or closed condition (FIGS. 21 and 22) to a second or open condition (FIG. 23) on its own, upon a sufficient increase in pressure within the drug reservoir 290. While this is similar to the seal 256 of FIGS. 16 and 17, the seal 292 of FIGS. 21-23 is different because it is configured to be movable between the closed and open conditions (i.e., it is reversibly deformable), rather than irreversibly moving from the closed condition to the open condition.

More particularly, the seal 292 of FIGS. 21-23 may be at least partially formed of an elastomeric material (e.g., a rubber material). The seal 292 is initially formed in its closed condition (FIGS. 21 and 22) in which it provides a complete barrier between the interior of the drug reservoir 290 and the outlet 252. When pressure within the drug reservoir 290 is increased to a sufficient level (e.g., by movement of the piston 254 toward the seal 292), a portion or end 294 of the seal 292 deforms to define an opening or fluid path through the seal 292 (FIG. 23), allowing a drug D in the interior of the drug reservoir 290 to flow through the opening and into the outlet 252. When pressure within the drug reservoir 290 decreases to a sufficient level, the deformed portion or end 294 of the seal 292 will return to its initial, closed condition, again preventing flow through the seal 292. The seal 292 of FIGS. 21-23 may, thus, be understood as and configured as a check valve or duck-bill valve or poppet valve or the like. When the seal is so configured (i.e., elastically or reversibly deformable), it is suitable for use in combination with an on-body injector in which a drug is to be intermittently or periodically conveyed from the drug reservoir over the course of a drug delivery routine, with the seal moving between closed and open conditions multiple times.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An on-body injector comprising:
a housing;
an adhesive pad associated with a lower surface of the housing and configured to be removably attached to a human body surface;
a drug reservoir positioned within the housing and including a deformable outlet;

a valve associated with the outlet and comprising first and second jaws configured to receive at least a portion of the outlet therebetween;
a release mechanism associated to the valve and comprising a filament formed of a shape memory alloy;
a needle fluidically connected to the outlet of the drug reservoir; and
a controller configured to control the on-body injector to execute a drug delivery routine, wherein the filament is configured to contract in order to move at least a portion of at least one of the first and second jaws with respect to the other one of the first and second jaws so as to move the valve from a first condition in which the first and second laws engage and deform the outlet so as to prevent fluid flow from the drug reservoir via the outlet to a second condition in which the valve allows fluid flow from the drug reservoir via the outlet.

2. The on-body injector of claim 1, wherein
the controller is configured to cause an electrical current to flow through the filament, and
the filament is configured to contract when said electrical current flows through the filament, thereby moving said at least a portion of said at least one of the first and second jaws with respect to the other one of the first and second jaws.

3. The on-body injector of claim 1, wherein the controller is configured to execute a drug delivery routine for a drug comprising pegfilgrastim.

4. The on-body injector of claim 1, wherein a portion of the drug reservoir is defined by a sidewall formed of a generally rigid material.

5. The on-body injector of claim 4, wherein
the drug reservoir includes an end associated with the sidewall, and
the outlet is associated with said end of the drug reservoir.

6. The on-body injector of claim 4, further comprising a piston configured to form a seal with the sidewall and to move through the drug reservoir toward said end of the drug reservoir during the drug delivery routine.

7. The on-body injector of claim 1, wherein the drug reservoir is formed of a generally flexible or deformable material.

8. The on-body injector of claim 7, wherein an interior of the housing is pressurized so as to apply a force to the drug reservoir.

9. The on-body injector of claim 7, wherein the drug reservoir is configured to be deformed by physical contact.

10. The on-body injector of claim 9, further comprising two surfaces, wherein
at least a portion of the drug reservoir is positioned between said two surfaces, and
at least one of said surfaces is configured to be moved toward the other surface so as to apply a compressive force to the portion of the drug reservoir positioned between said surfaces.

11. The on-body injector of claim 10, wherein each surface is configured to move toward the other surface so as to apply said compressive force to the portion of the drug reservoir positioned between said surfaces.

12. The on-body injector of claim 10, wherein each surface is configured as a flat plate.

13. The on-body injector of claim 9, wherein the controller is configured to cause said physical contact to be applied to the drug reservoir when the valve is in the first condition.

14. The on-body injector of claim 9, wherein the controller is configured to cause said physical contact to not be applied to the drug reservoir when the valve is in the first condition.

15. The on-body injector of claim 1, wherein the outlet is configured as a tube, and the valve is configured to press a portion of the tube against an opposing portion of the tube when the valve is in the first condition.

16. The on-body injector of claim 1, wherein the outlet is formed of an elastomeric material.

17. The on-body injector of claim 1, wherein the outlet is formed of a polyvinyl chloride material.

18. The on-body injector of claim 1, wherein the release mechanism is configured to move the valve between said first and second conditions.

19. The on-body injector of claim 1, wherein the filament is secured to one of the first and second jaws.

\* \* \* \* \*